US00PP22334P3

(12) United States Plant Patent
Egger

(10) Patent No.: US PP22,334 P3
(45) Date of Patent: Dec. 13, 2011

(54) *NEPETA* PLANT NAMED 'BLUE DRAGON'

(50) Latin Name: ***Nepeta* hybrid**
Varietal Denomination: Blue Dragon

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 157 days.

(21) Appl. No.: 12/653,644

(22) Filed: Dec. 14, 2009

(65) Prior Publication Data

US 2011/0145958 P1 Jun. 16, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Wendy C Haas

(74) *Attorney, Agent, or Firm* — Klarquist Sparkman, LLP

(57) ABSTRACT

A new and distinct form of *Nepeta* hybrid characterized by medium height, strongly upright habit, large violet flowers, and vigor. It is an ideal middle or back of the border perennial for full sun.

1 Drawing Sheet

Botanical denomination: *Nepeta* hybrid.
Variety designation: 'Blue Dragon'.

BACKGROUND OF THE INVENTION

The present invention relates to a new and distinct cultivar of *Nepeta,* given the name, 'Blue Dragon'. *Nepeta* is in the family Lamiaceae. This plant originated from a planned breeding cross between *Nepeta yunnanensis,* as the seed parent, and *Nepeta nervosa,* as the pollen parent. Four seedlings resulted from the cross. This new cultivar was selected as it was more dwarf than the seed parent *Nepeta yunnanensis* with larger flowers and a strongly upright habit rather than sprawling. In addition, the new cultivar doesn't run like some *N. yunnanensis* described online. Compared to the pollen parent, *Nepeta nervosa,* the new cultivar is taller, with larger flowers, and larger and deeper green leaves. Compared to *Nepeta parnassica*, the new cultivar has larger, darker blue flowers and is shorter in habit.

*Nepeta* 'Blue Dragon' is unique in its combination of medium height, strongly upright habit, large violet flowers, and vigor. It is an ideal middle or back of the border perennial for full sun.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 2:
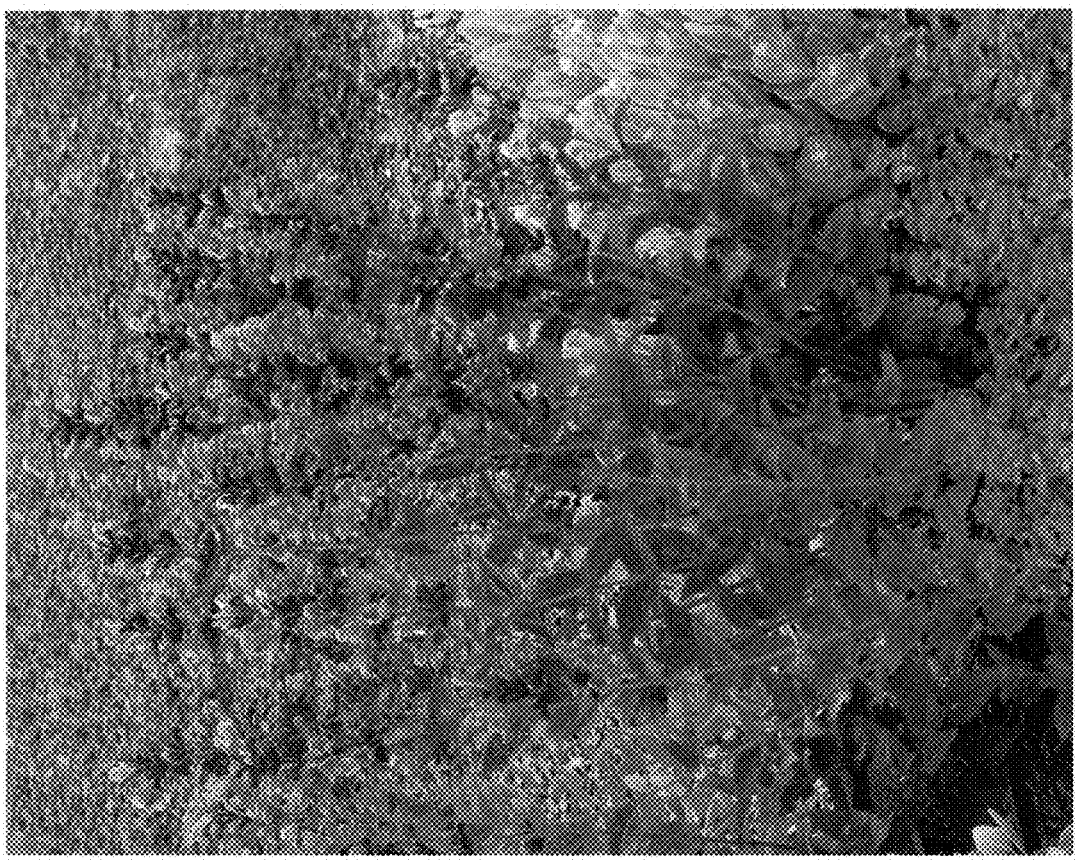
FIG. 2 shows a two year old *Nepeta* 'Blue Dragon' in bloom growing in full sun in the trail bed in June in Canby, Oreg.
Figure 1:
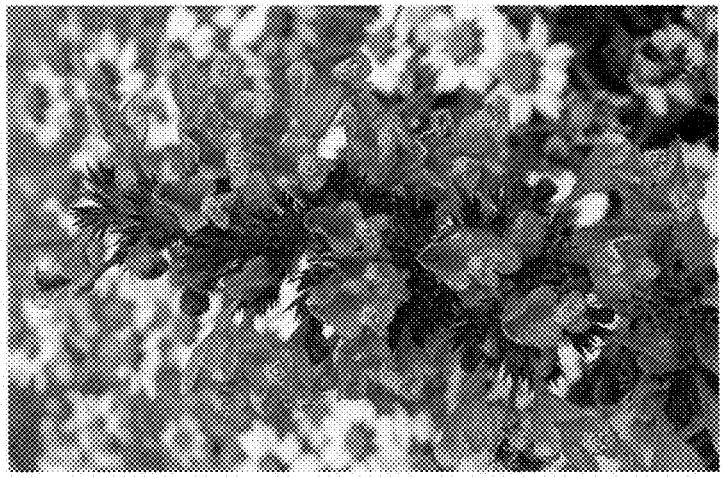
FIG. 1 shows a close up of the flower of *Nepeta* Blue Dragon.

The following is a detailed description of the new *Nepeta* cultivar based on observations of a four-year-old specimen grown outside in the ground in the trial beds in Canby, Oreg. The color descriptions are all based on The Royal Horticultural Society Colour Chart, 5$^{th}$ edition.

Plant:
- *Type.*—Herbaceous perennial.
- *Form.*—Upright clumping.
- *Cold hardiness.*—USDA Zone 5-10.
- *Size.*—Grows to 84 cm wide and 89 cm high.
- *Vigor.*—Excellent.
- *Stem number.*—30 stems from the crown.
- *Stem.*—Upright, grows to 62 cm long and 10 mm wide (at the base), internodes grow to 7 cm long, with side branches at 12 degree angles off the main stem, pubescent, Yellow Green 146C, square in cross section.
- *Rooting.*—Plants root easily from stem cuttings.

Leaf:
- *Type.*—Simple, aromatic.
- *Arrangement.*—Opposite.
- *Shape.*—Ovate.
- *Venation.*—Pinnate.
- *Margins.*—Coarsely serrate.
- *Apex.*—Acuminate.
- *Base.*—Cordate-auriculate.
- *Stipules.*—None.
- *Blade size.*—Grows to 12 cm long and 7 cm wide.
- *Surface texture.*—Pubescent on both sides.
- *Petiole.*—Grows to 1 cm long and 1 mm wide, pubescent, Yellow Green 147B.
- *Leaf color.*—Topside green N137D with main vein Yellow Green 147B, bottom side Yellow Green 147B.

Inflorescence:
- *Type.*—Terminal many flowered verticillasters in opposite cymes.

*Number of flowers.*—Nine to 27 per cyme.

*Size of inflorescence.*—Grows to 32 cm long and 10 cm wide.

*Peduncle.*—Grows to 34 cm long and 5 mm wide, pubescent, Yellow Green 146C.

*Pedicel.*—Sessile.

*Bloom period.*—May to September in Canby, Oreg.

Flower bud:

*Size.*—32 mm long and 11 mm wide at the widest point prior to opening.

*Description.*—Irregular teardrop, flattened dorsally.

*Surface.*—Pubescent.

*Color.*—Violet Blue 90B.

Flower:

*Type.*—Zygomorphic.

*Shape.*—Bilabiate, funnel form.

*Corolla description.*—43 mm long and to 18 mm wide; tube 18 mm long, throat 15 mm long and 12 mm wide, flattened dorsally, pouched on bottom; 2 upper lobes orbicular, overlapping, 8 mm long and 8 mm wide, obtuse, entire; two side lobes, orbicular, 5 mm long and 6 mm wide, entire, obtuse; the bottom lobe 6 mm long and 10 mm wide, orbicular on a short limb, in two cupped parts, entire, obtuse; pubescent outside, glabrous inside except bottom lobe which has long pubescence in the center; color inside Violet Blue 90B, outside Violet Blue 90C except on bottom lobe where inside color is spotted Purple Violet N81A, Violet Blue 90A, and Violet N88A on a light background, Violet 85C.

*Calyx description.*—Funnel form, 5 lobed, 11 mm long and 5 mm wide, lobes dorsal flattened, narrow and deeply cut, acuminate, entire, strongly pubescent outside, glabrous inside; upper 3 lobes spreading, 5 mm long and 1 mm wide; lower 2 lobes together 4 mm long and 1 mm wide, Greyed Purple N186A.

*Pistil description.*—1, 36 mm long, ovary 1 mm long; style 34 mm long, Violet N85C; stigma 1 mm long, Violet 86A.

*Stamen description.*—4, 2 upper filaments with sometimes sterile anthers 10 mm long and Violet 86B, 2 lower filaments fertile, 18 cm long, and Violet 86C; sterile anthers Grey Brown N199D, fertile anthers Violet 86A, pollen White 155B.

*Fragrance.*—Herbal.

*Lastingness.*—A spike blooms for about 3 weeks on the plant.

Fruit and seed: 4 nutlets, Greyed Purple N186A.

Pests and diseases: Insect and disease resistance is believed to be typical for the genus. *Nepeta* are reputed to be disease resistant plants.

I claim:

1. A new and distinct form of *Nepeta* plant substantially as shown and described.

* * * * *

UNITED STATES PATENT AND TRADEMARK OFFICE

CERTIFICATE OF CORRECTION

PATENT NO. : PP22,334 P3
APPLICATION NO. : 12/653644
DATED : December 13, 2011
INVENTOR(S) : Janet N. Egger It is certified that error appears in the above-identified patent and that said Letters Patent is hereby corrected as shown below:

On the Title Page, Item (56):

The following should be added:

--(56) References Cited, U.S. Patent No. PP18,904 P2 06/2008 Core--

Signed and Sealed this
Thirteenth Day of August, 2013

Teresa Stanek Rea
*Acting Director of the United States Patent and Trademark Office*